(12) United States Patent
Wilmot et al.

(10) Patent No.: US 7,811,254 B2
(45) Date of Patent: Oct. 12, 2010

(54) AUTOINJECTOR WITH NEEDLE DEPTH ADAPTER

(75) Inventors: John G. Wilmot, Mount Airy, MD (US); Robert L. Hill, Abingdon, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 128 days.

(21) Appl. No.: 11/788,823

(22) Filed: Apr. 20, 2007

(65) Prior Publication Data

US 2008/0097312 A1 Apr. 24, 2008

Related U.S. Application Data

(60) Provisional application No. 60/852,493, filed on Oct. 18, 2006.

(51) Int. Cl.
*A61M 5/00* (2006.01)

(52) U.S. Cl. ...................... 604/117; 604/171

(58) Field of Classification Search ................ 604/117
See application file for complete search history.

(56) References Cited

U.S. PATENT DOCUMENTS

| | | | | |
|---|---|---|---|---|
| 2,626,604 A | 1/1953 | Nadeau | ................ | 138/218 |
| 2,674,246 A | 4/1954 | Bower | ................ | 128/215 |
| 2,701,566 A | 2/1955 | Krug | ................ | 128/218 |
| 2,866,458 A | 12/1958 | Hein, Jr. | ................ | 128/218 |
| 3,380,449 A | 4/1968 | Sarnoff | ................ | 128/218 |
| 3,797,489 A | 3/1974 | Sarnoff | ................ | 128/218 |
| 3,820,542 A | 6/1974 | Hurschman | ................ | 128/218 |
| 3,882,863 A | 5/1975 | Sarnoff et al. | ................ | 128/218 |
| 4,529,403 A | 7/1985 | Kamstra | ................ | 604/136 |
| 4,553,962 A | 11/1985 | Brunet | ................ | 604/198 |
| 4,710,171 A | 12/1987 | Rosenberg | ................ | 604/117 |
| 4,723,937 A | 2/1988 | Sarnoff et al. | ................ | 604/90 |
| 4,988,339 A | 1/1991 | Vadher | ................ | 604/197 |
| 5,102,393 A | 4/1992 | Sarnoff et al. | ................ | 604/136 |
| 5,190,526 A | 3/1993 | Murray et al. | ................ | 604/110 |
| 5,263,934 A | 11/1993 | Haak | | |
| 5,358,489 A | 10/1994 | Wyrick | | |
| 5,391,151 A | 2/1995 | Wilmot | ................ | 604/139 |
| 5,417,662 A | 5/1995 | Hjertman et al. | ................ | 604/117 |
| 5,425,715 A | 6/1995 | Dalling et al. | ................ | 604/136 |
| 5,873,856 A | 2/1999 | Hjertman et al. | ................ | 604/117 |
| 6,213,977 B1 | 4/2001 | Hjertman et al. | ................ | 604/117 |
| 6,312,412 B1 | 11/2001 | Saied et al. | ................ | 604/191 |
| 6,423,034 B2 | 7/2002 | Scarfone et al. | | |
| 6,689,118 B2 | 2/2004 | Alchas et al. | ................ | 604/506 |
| 6,746,429 B2 | 6/2004 | Sadowski et al. | ................ | 604/201 |
| 6,764,471 B2 | 7/2004 | Lee | | |
| 6,843,781 B2 | 1/2005 | Alchas et al. | | |
| 6,971,999 B2 | 12/2005 | Py et al. | | |
| 7,011,649 B2 | 3/2006 | De La Serna et al. | ......... | 604/197 |
| 7,056,302 B2 | 6/2006 | Douglas | ................ | 604/136 |
| 7,083,599 B2 | 8/2006 | Alchas et al. | | |
| 2004/0254543 A1 | 12/2004 | Griffiths | | |
| 2005/0049542 A1 | 3/2005 | Sigg et al. | | |

(Continued)

*Primary Examiner*—Nicholas D Lucchesi
*Assistant Examiner*—Jason Flick
(74) *Attorney, Agent, or Firm*—Waddey & Patterson, P.C.; Edward D. Lanquist, Jr.; Ryan D. Levy (57) ABSTRACT

An autoinjector useful for, inter alia, providing an injection of liquid medicament is disclosed, which includes a needle depth adapter for achieving a desired injection depth.

48 Claims, 2 Drawing Sheets

U.S. PATENT DOCUMENTS

| | | |
|---|---|---|
| 2005/0171477 A1* | 8/2005 | Rubin et al. ............... 604/156 |
| 2005/0180952 A1* | 8/2005 | Pettis et al. ............... 424/85.2 |
| 2005/0187519 A1 | 8/2005 | Harris et al. |
| 2005/0203459 A1 | 9/2005 | Alchas |
| 2005/0256499 A1 | 11/2005 | Pettis et al. |
| 2006/0129122 A1 | 6/2006 | Wyrick |
| 2006/0173408 A1* | 8/2006 | Wyrick ...................... 604/110 |

* cited by examiner

FIG. 3    FIG. 4    FIG. 5

AUTOINJECTOR WITH NEEDLE DEPTH ADAPTER

The present application is a continuation of and claims benefit of U.S. provisional patent application Ser. No. 60/852,493 entitled "AUTOINJECTOR WITH NEEDLE DEPTH ADAPTER" filed Oct. 18, 2006 which is hereby incorporated by reference. Additionally all patents and publications described or discussed herein are hereby incorporated by reference in their entireties.

BACKGROUND OF THE INVENTION

1. Technical Field

The present invention relates to an autoinjector with a novel needle depth adapter useful for applications including administering injections to both humans and animals. More particularly, the present invention relates to autoinjectors capable of injecting medicaments into a precise location within the subject. Furthermore, this invention can be specially adapted for subcutaneous injections and also includes a novel method of administering medicaments to a desired depth within a patient.

2. Background Art

Autoinjectors have become quite popular and have experienced widespread use due to a variety of advantages autoinjectors have over typical manual syringe injectors. Essentially, an autoinjector is an automatic injection system which is designed to deliver a specific dosage of a liquid medicament into an individual. Through their pen-styled design, autoinjectors are fairly simple to use and often have design characteristics enabling an individual to administer a self-injection. The majority of autoinjectors in production today are spring-loaded autoinjectors which provide an individual with less hesitation in self-administering liquid medicaments than would a manual syringe and needle. Furthermore, automatic injectors are much simpler to use in times of stress, pain, or other medical ailments and require less concentration than would a standard manual syringe and needle.

An additional advantage of autoinjectors is that these injectors contain a specific size dose of a liquid medicament sealed within and can be stored for a significant duration. Despite the capability for being stored for a significant duration, the autoinjector is still able to provide an immediate injection even under severe medical stress. Furthermore, automatic injectors will deliver a previously determined dosage of the medicament upon activation, thus precluding the need to measure the specific amount of medicament needed at the time the injection is administered.

Depending on the type of drug and the ailment which the medicament is designed to alleviate, the autoinjector is designed to penetrate to a certain depth. Commonly, most autoinjectors are used for intramuscular injections and have only most recently been designed to provide for subcutaneous injections. Specifically, certain medicines, especially medicines for alleviating migraine headaches, must be injected in the subcutaneous region of a patient rather than have the injection site be at an intramuscular location. The key design consideration in creating an autoinjector for a subcutaneous injection is to attempt to insure that the needle of the autoinjector does not penetrate to a depth beyond the subcutaneous region of the patient. For example, in Sarnoff et al., U.S. Pat. No. 5,102,393, an autoinjector is disclosed which claims to be convertible from an intramuscular to subcutaneous mode of injection. The autoinjector of the '393 patent is taught to have the capability of being actuated in a manner so as to cause virtually no compression of the subcutaneous tissue under the skin at the injection site of the user. For using the autoinjector of the '393 patent in a subcutaneous mode, another device is secured to the autoinjector which attempts to preclude the needle from extending substantially beyond the subcutaneous tissue.

In U.S. Pat. No. 5,873,856, Hjertman et al., a device is disclosed which claims to have a limited depth penetration needle housing. The '856 patent teaches a device which can be adjusted for specific depths of penetration which claims to include a subcutaneous depth of penetration. Furthermore, the disclosure teaches a device where one can readily adjust the needle penetration depth between different pre-set values.

In Saied et al., U.S. Pat. No. 6,312,412, injectors are disclosed which can provide for either intramuscular or subcutaneous injection. The specific injector of the '412 patent includes means for adjusting the medication needle so that the medication needle can be inserted to varying depths within the patient.

De La Serna et al. (U.S. Pat. No. 7,011,649) describes a syringe cartridge which may include an adjustable tip which will allow a user to easily adjust the injection depth for the desired application.

Unfortunately, autoinjectors produced by the prior art processes are not effective for administering subcutaneous injections at an exact and repeatable depth of penetration. The injectors generally available do not have as tight a range of penetration depth as is desired, and furthermore, include needle tips which are adjustable and provide for another variable which can lead to an incorrect penetration depth in times of emergency trauma. In addition, prior art subcutaneous injectors do not include a method wherein the depth of penetration is limited to a small range of penetration depths.

What is desired, therefore, is an autoinjector which has a tight range regarding the needle's depth of penetration wherein the medicament contained within the autoinjector is injected into a specific location within the patient, including the subcutaneous region. Indeed a combination of characteristics including a much more precise range of penetration depths as well as simplicity of use have been found to be necessary for the use of autoinjectors for administering specific medicament into the subcutaneous region of a subject. Also desired is the method for providing more exact injections, including injections within the subcutaneous region.

SUMMARY OF THE INVENTION

The present invention provides an autoinjector which is uniquely capable of providing injections, preferably subcutaneous injections, with improved precision. The inventive autoinjector utilizes a needle depth adapter to provide injection depths with a combination of accuracy and precision not heretofore seen. In addition, the autoinjector with needle depth adapter can include a variety of size needle depth adapters to provide an autoinjector of varying, precise injection depths and which can be readily and easily manufactured.

More particularly, the autoinjector with needle depth adapter can provide injections in the subcutaneous region wherein the injection is at a depth of from about 0.15 inches to about 0.30 inches, and more preferably of from about 0.2 inches to about 0.25 inches within the subject. An important characteristic of the autoinjector when intended for self-administered injections is that the autoinjector comes preassembled with a fixed injection depth thereby limiting the possibility of injecting at erroneous depths during times of trauma.

The inventive autoinjector with needle depth adapter should have a needle depth adapter comprised of a material which includes thermoplastics, polymers, hydrocarbon polymers or cellulosic compositions as well as deformable metals to provide for the desired depth of injection in a very precise range. Furthermore, the needle depth adapter is comprised of a deformable material to eliminate tight tolerances in manufacturing while still providing for a very controlled injection depth. Yet furthermore, by use of a deformable material in forming the needle depth adapter of the autoinjector, the needle depth adapter can dissipate excessive mechanical force created by the powering mechanism of the autoinjector, and thus, can eliminate autoinjector failure wherein the force-providing component is too strong.

More particularly, the needle depth adapter is in close proximity to the needle hub, with the needle depth adapter having a partition for the extension of the needle therethrough. As such, the needle depth adapter can be contoured to align closely with the needle hub and will move with the cartridge assembly toward the proximal end of the autoinjector upon activation of the autoinjector.

The autoinjector with needle depth adapter is especially useful for providing the subcutaneous injection of medicaments where the medicament's effectiveness depends on the location of injection within the patient. With the preferred small range of from about 0.20 inches to about 0.25 inches for subcutaneous injections, the autoinjector with needle depth adapter is suitable for medicaments such as sumatriptan, rizatriptan, frovatriptan, zolmitriptan, naratriptan, and loperamide hydrochloride. Furthermore, a variety of other drugs, including drugs of the epinephrine variety can be loaded into the autoinjector and injected also to a precise depth.

Advantageously, the autoinjector with needle depth adapter provides a method for administering injections at a much more precise injection depth making this method highly suitable for use in emergency trauma situations.

An object of the invention, therefore, is an autoinjector with a needle depth adapter having characteristics which enable it to be employed for subcutaneous injections which can be self-administered.

Another object of the invention is an autoinjector having improved precision with regard to depth of needle penetration within the subject to be injected.

Yet another object of the invention is an autoinjector having a needle depth adapter so that the depth of penetration of the needle is located within the subcutaneous region of the subject.

A further object of the invention is an autoinjector having a punctureable needle sheath wherein the sheath does not have to be removed prior to administering the injection.

Another object of the invention is an autoinjector for injecting sumatriptan into the subcutaneous region of the subject.

Still another object of the invention is an autoinjector with needle depth adapter wherein the needle depth adapter is deformable and is easily assembled into the autoinjector without the need for precise interface geometry.

Yet another object of the invention is an autoinjector with a needle depth adapter wherein the depth of the injection is fixed so as to reduce the possibility of erroneous depth injections.

Another object of the invention is a method of providing injections with improved precision which can be self-administered by an individual.

These aspects and others that will become apparent to the artisan upon review of the following description can be accomplished by providing an automatic injector with a needle depth adapter wherein the needle depth adapter limits the forward progression of the needle, and thus, controls the depth of injection within the patient. The inventive autoinjector with needle depth adapter advantageously can provide precise injections, including subcutaneous injections in the range of from about 0.15 inches to about 0.30 inches and more preferably of from about 0.20 inches to about 0.25 inches.

Preferably, the needle depth adapter is comprised of a deformable material which can include a variety of polymers as well as deformable metals which will limit the forward progression of the needle and can also dissipate excess force created by the spring-type mechanism within the autoinjector. Advantageously, the needle depth adapter can range from about 0.4 inches to about 0.6 inches in width and from about 0.2 inches to about 0.4 inches, preferably about 0.3 inches in length although it can be modified to include greater or smaller lengths depending on the specific desired depth of injection. Advantageously, the automatic injector with needle depth adapter includes a fixed injection depth of the final injector product thereby eliminating the potential for erroneous injection depths which can occur from adjustable autoinjector types.

Furthermore, the method for producing more precise injections includes the use of the needle depth adapter to preclude the forward movement of the needle thereby precisely limiting the depth of injection to a specifically tailored range.

It is to be understood that both the foregoing general description and the following detailed description provide embodiments of the invention and are intended to provide an overview or framework of understanding of the nature and character of the invention as it is claimed.

DETAILED DESCRIPTION OF THE PREFERRED EMBODIMENTS

Figure 1:
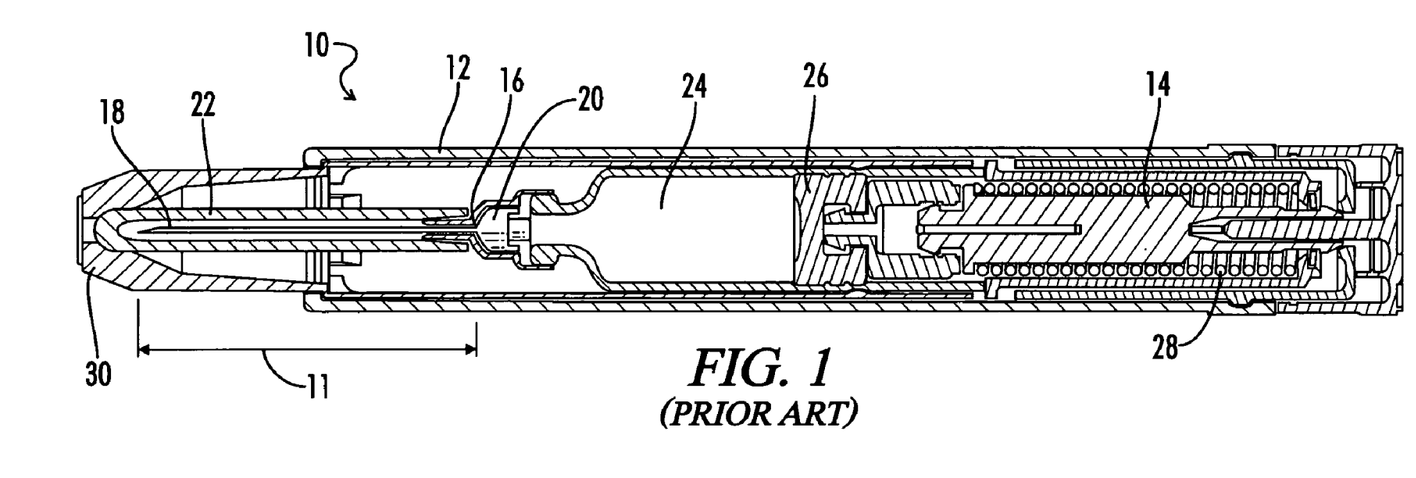
FIG. 1 is a longitudinal sectional view of a prior art automatic injector in the non-actuated position.

In general automatic injector 10 of the prior art typically includes housing 12, power assembly 14, and needle cartridge assembly 16 as illustrated in FIG. 1. Automatic injector 10 may further include needle 18 attached by needle hub 20 with needle 18 being shrouded by buckling sheath 22.

Needle cartridge assembly 16 is slidingly located within housing 12 of autoinjector 10 and contains the liquid medicament intended for injection within the patient. Specifically, chamber 24 contains the liquid medicament wherein upon activation, plunger 26 will force liquid medicament out through the piercing end of needle 18. Needle hub 20 holds needle 18 in a fixed position with chamber 24 so that the liquid medicament can communicate from chamber 24 to needle 18 and out through the piercing end of needle 18 and into a subject.

As further illustrated in FIG. 1, power assembly 14 includes compressed spring 28 which possesses the potential energy capable of thrusting the needle out of autoinjector 10 and also infusing the liquid medicament from chamber 24 out through piercing end of needle 18. In the inactivated condition, needle 18 is contained within autoinjector 10, the length as illustrated by needle containment length 11. Otherwise stated, needle containment length 11 is the length of needle 18 within autoinjector 10 prior to utilizing autoinjector 10 to dispense a medicament.

Figure 2:
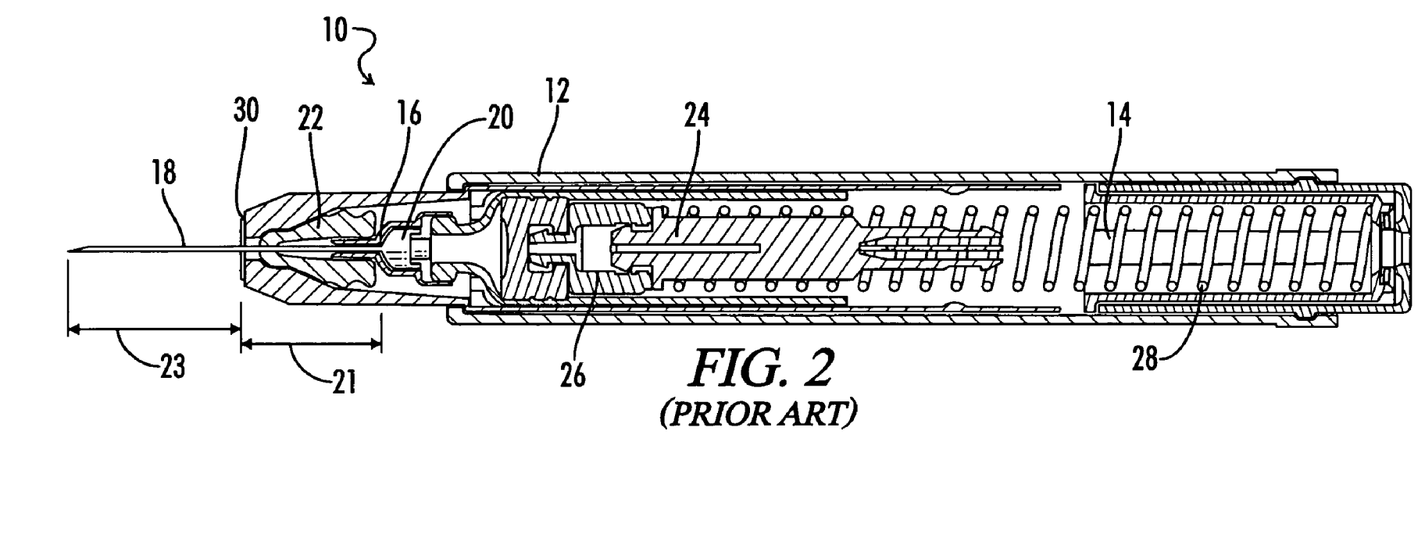
FIG. 2 is a longitudinal sectional view of the prior art automatic injector of FIG. 1 in the actuated position.

When using autoinjector 10 of the prior art, the safe pin of autoinjector 10 is removed and subsequently autoinjector 10 is pressed at proximal end 30 against the patient for which the injection is to be administered. When injector 10 is actuated, compressed spring 28 of power assembly 14 decompresses and propels needle assembly 16 toward proximal end 30 of injector 10. As illustrated in FIG. 2, needle assembly 16 including needle 18 and chamber 24 as well as plunger 26 are propelled forward under the influence of the decompression of spring 28. With this forward motion, buckling sheath 22 compresses between proximal end 30 of autoinjector 10 and needle assembly 16. The piercing end of needle 18 breaks through buckling sheath 22 and emanates out of proximal end 30 of autoinjector 10. At the instant needle 18 reaches its extended length, the medicament contained in chamber 24 is pushed forward by plunger 26 and thus exits the piercing end of needle 18 and into the subject.

The depth to which needle 18 penetrates the patient is determined by the forward progression of needle 18 out of proximal end 30 of autoinjector 10 and by the extent of buckling sheath 22. When needle 18 is in the foremost position, needle 18 is precluded from going more forward by the force provided by buckling sheath 22 against the inside of proximal end 30 of autoinjector 10. Specifically, buckling sheath 22 buckles under the force provided from decompressing spring 28 of power assembly 14 and thereby determines the extended length of needle 18 of prior art autoinjector 10. Compressed sheath length 21 is the length of buckling sheath 22 after buckling and thus maintains a portion of needle 18 within autoinjector 10, a length about equal to compressed sheath length 21. By buckling sheath 22 buckling to compressed sheath length 21, needle 18 only extends to extended needle length 23, as a length of needle 18 about equal to compressed sheath length 21 is maintained within autoinjector 10.

When used for intramuscular injections, the extended length of the needle, extended needle length 23, is of from about 0.7 inches to about 0.9 inches determined through the buckling of the sheath at the proximal end of the prior art autoinjector. Much more precise injection depths are difficult to achieve as the buckling of the sheath can vary slightly from one autoinjector to another. Generally, prior art autoinjectors with buckling sheaths are difficult to produce wherein the range of injection depth from one autoinjector to another varies less than about 0.1 inches. Moreover, when autoinjectors are used to administer medicaments in the subcutaneous region of a patient, a buckling sheath used for determining the needle depth is quite problematic as injections within the subcutaneous region require a very precise injection location and have a low tolerance for injections administered outside of this location.

Figure 3:
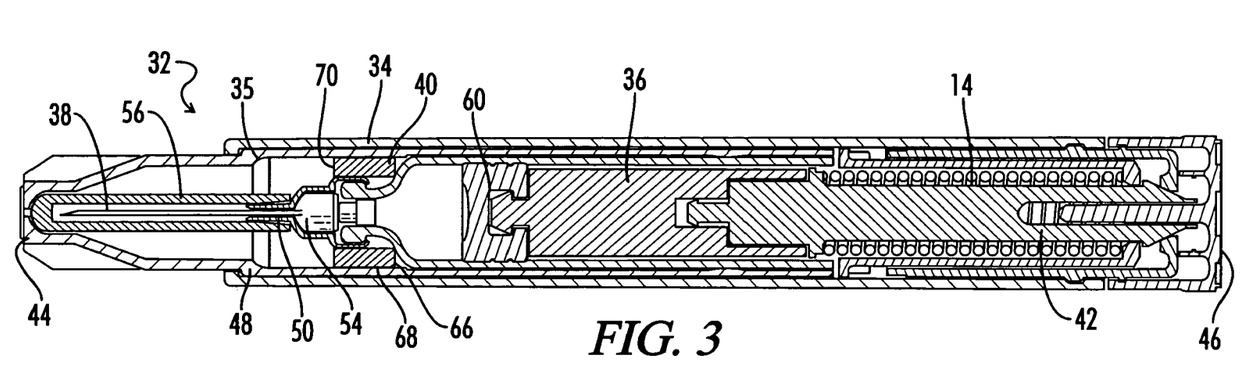
FIG. 3 is a longitudinal sectional view of an automatic injector according to the present invention in the non-actuated position.

As illustrated in FIG. 3, autoinjector 32 of the present invention includes housing 34, cartridge assembly 36, needle 38, needle depth adapter 40, and power providing assembly 42.

Housing 34 includes an outer tube-type design with proximal end 44 and distal end 46. Housing 34 of autoinjector 32 is designed so that proximal end 44 is the end nearest to the injection site of the subject, as distal end 46 is the end most distant from the injection site. Furthermore, housing 34 may be constructed of any rigid material including metals, alloys, polymer-type materials, glass, as well as ceramic composites. Preferably, housing 34 is comprised of a rigid material so as to be able to withstand the mechanical stress received upon the actuation of power providing assembly 42. Most often, a polymer or plastic material is suitable for housing 34 as these materials provide sufficient strength while also possessing a high ratio of strength to density allowing for the creation of a relatively lightweight autoinjector.

In one embodiment, housing 34 of autoinjector 32, is designed so that cartridge container 48 fits within the inner diameter of housing 34. Cartridge container 48 is designed so as to maintain a sliding configuration within housing 34 upon application of force to the distal end of cartridge container 48. As such, the outer diameter of cartridge container 48 is about slightly less than the inner diameter of housing 34. Both housing 34 and cartridge container 48 can be designed in a variety of sizes and configurations dependent upon the specific use desired for the autoinjector. For example, in designing autoinjectors for easy portability, the autoinjector may be designed in a longer, slimmer fashion so as to be easily carried with the user at all times. Furthermore, when a large quantity of medicament is required, the autoinjector and cartridge container can be designed so as to accommodate the large amount of medicament.

Cartridge container 48 may be retained within housing 34 of autoinjector 32 in a variety of ways. In one embodiment, cartridge container 48 may be retained within housing 34, by a return flange to maintain cartridge container 48 within autoinjector 32.

Figures 4, 5:
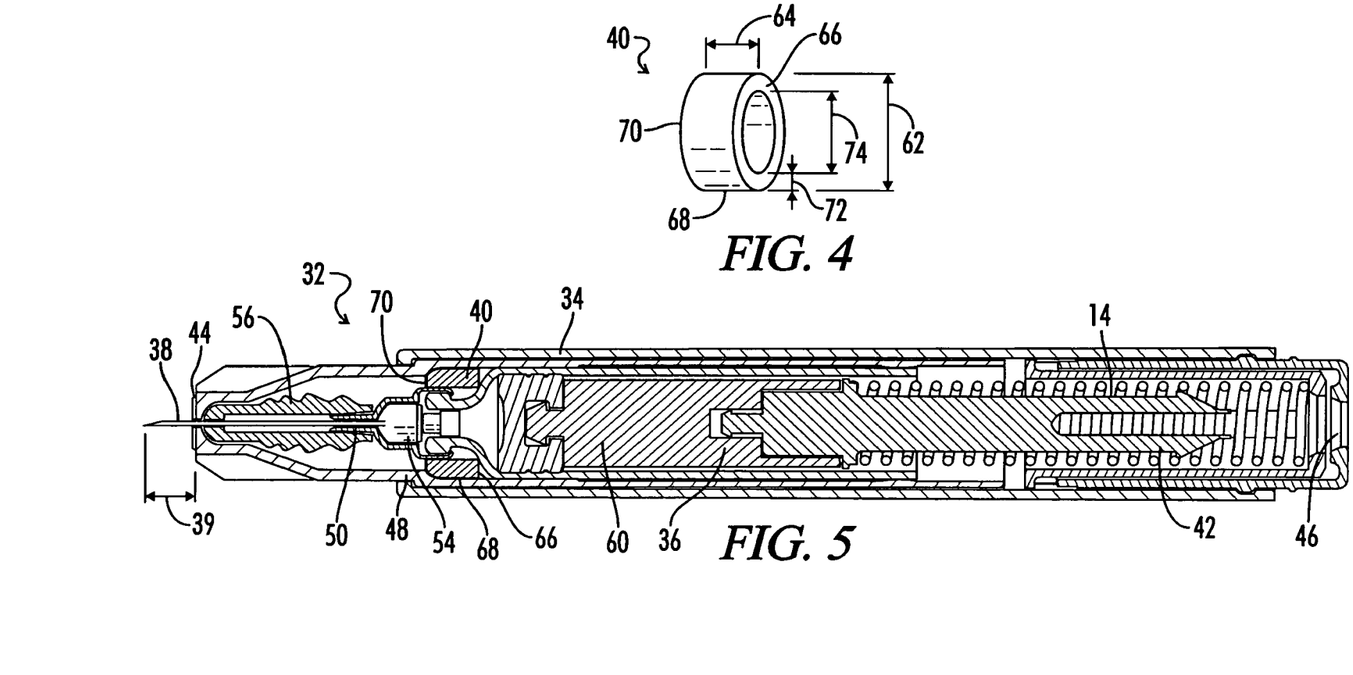
FIG. 4 is a view of a needle depth adapter according to the present invention.
FIG. 5 is a longitudinal sectional view of an automatic injector according to the present invention in the actuated position.

Furthermore, in the aforementioned embodiment, cartridge container 48 has abutment surface 35 for abutting needle depth adapter 40. In embodiments not including cartridge container 48, the housing assembly may contain an abutment surface for abutting needle depth adapter 40. Abutment surface 35 may be angled as illustrated in FIG. 3 and FIG. 5 or in other embodiments may be rounded or flat. Typically, abutment surface 35 is angled so as to only contact and compress the corner of the needle depth adapter upon abutment.

Cartridge assembly 36 is moveably situated within cartridge container 48 and thus will move toward proximal end 44 of autoinjector 32 upon sufficient force provided by power providing assembly 42. Cartridge assembly 36 is designed so that the exterior diameter of cartridge assembly 36 is slightly less than that of the interior diameter of cartridge container 48 so that cartridge assembly 36 can move in a longitudinal direction without excessive friction. Furthermore, the medicament is contained within cartridge assembly 36 and can be designed to accommodate a variety of medicament types including larger or smaller quantities as well as high or low viscosity medicaments. Typically, cartridge assembly 36 is comprised of a rigid material often including glass, metals, polymers, thermoplastics, or composites. As the medicament is contained within cartridge assembly 36, the cartridge assembly is designed so as to preclude the absorption of the contained medicament as well as to preclude the migration of the medicament out of cartridge assembly 36.

The proximal end of cartridge assembly 36 is designed to connect to needle assembly 50 which is comprised of needle 38, needle hub 54, and punctureable sheath 56. Needle hub 54 has a first connection point for connecting to the proximal end of cartridge assembly 36 and a second connection point for receiving the attachment end of needle 38. Needle hub 54 may connect to the cartridge assembly in multiple ways including, but not limited to, a screw-type attachment, a pressure fit, or even an adhesive connection between the needle hub 54 and cartridge assembly 36. Furthermore, needle hub 54 may preferably be spun or crimped into place about the end of cartridge assembly 36 so that a secure connection is achieved. Generally, needle hub 54 may communicate needle 38 to cartridge assembly 36 in the manner commonly taught in U.S. Pat. No. 3,380,449, the disclosure of all of which is hereby incorporated by reference into the present specification.

Needle 38 of needle assembly 50 may be of any design suitable for the injection of a medicament into a patient. For example, needle 38 may have an interior diameter suitable for either low viscosity or high viscosity medicament, may be of either an oval or circular cross-sectional design and can also be of a variety of different lengths depending upon the size and intended use of the novel autoinjector.

Punctureable sheath 56 functions to maintain sterility of needle 38 and may be comprised of a polymer, plastic, or suitable metal material such as aluminum. The distal portion of punctureable sheath 56 is attached to needle hub 54. This attachment may be by pressure fitting, shrinking, folding, screw type, or adhesion wherein the complete encompassing of needle 38 by punctureable sheath 56 provides for an enduring sterile environment for needle 38. In a preferable arrangement, punctureable sheath 56 may be elastically fit to needle hub 54 by the inherent elastic characteristics of sheath 56, as the open end of sheath 56 may be stretched to fit over a portion of needle hub 54. Advantageously, punctureable sheath 56 does not require specific design criteria or as precise manufacturing as the prior art buckling sheath as punctureable sheath 56 is not responsible for controlling the depth of penetration of the needle of the autoinjector. As such, punctureable sheath 56 may be comprised of an extremely thin material or can be designed to more closely guard needle 38 thereby being able to better maintain a sterile environment around the needle while providing a compact autoinjector design.

Needle depth adapter 40 is located within cartridge container 48 in contact with needle hub 54 at the proximal end of cartridge assembly 36 and has an opening for needle 38 to extend therethrough. Depth adapter 40 is moveable with needle hub 54 and will move toward the proximal end of the autoinjector upon the application of mechanical force by power providing assembly 42.

FIG. 4 illustrates needle depth adapter 40 in one embodiment having an annular shape. For limiting the needle depth for subcutaneous injections, needle depth adapter 40 has a longitudinal length 64 which is from about 0.2 inches to about 0.4 inches and more preferably about 0.27 inches to about 0.33 inches in length. Radial exterior diameter 62 is designed so that exterior diameter 62 is less than the interior diameter of cartridge container 48 and is typically from about 0.4 inches to about 0.6 inches and more preferably from about 0.50 inches to about 0.52 inches.

Furthermore, distal end 66 of needle depth adapter 40 is in contact with the proximal end of cartridge assembly 36. Generally, distal end 66 of needle depth adapter 40 is perpendicular to exterior surface 68 of needle depth adapter 40 providing for a flat and even surface for contacting cartridge assembly 36. Additionally, abutting side 70 of needle depth adapter 40 may be in a perpendicular relation to exterior surface 68 and thus parallel to distal surface 66 providing a cylindrical-type shape to needle depth adapter 40.

Typically, needle depth adapter 40 has a ratio of exterior diameter 62 to longitudinal length 64 of greater than about 1. Furthermore, interior diameter 74 is of from about 0.2 to about 0.4 and preferably of from about 0.25 inches to about 0.35 inches to accommodate the extension of the proximal end of cartridge assembly 36 therethrough. Internal diameter 74 must be at least large enough for needle 38 to extend therethrough and can optionally be designed even larger so that a substantial portion of cartridge assembly 36 extends into the interior of needle depth adapter 40. As such, radial thickness 72 may be varied to accommodate a variety of autoinjector designs while still providing for a precise depth of injection. Most often, radial thickness 72 is of from about 0.05 inches to about 0.18 inches and preferably from about 0.10 inches to about 0.12 inches. Additionally, the needle depth adapter can also have a ratio of longitudinal length 64 of the needle depth adapter as measured from the distal surface to the proximal surface, to radial thickness 72 of greater than about 2, and preferably about 3.

Needle depth adapter 40 can be comprised of a variety of materials including thermoplastics, polymers, hydrocarbon polymers, deformable metals, cellulosic compositions and combinations thereof. Preferably, the material used for needle depth adapter 40 is a deformable material which is defined as material which can experience a change in shape due to the application of force. The choice of deformable materials is to negate the need to design precise interface geometry with tight tolerances when assembling autoinjector 32. Furthermore, the use of a deformable material for needle depth adapter 40 provides for the absorption of excess force created by power providing assembly 42. In a preferable embodiment, needle depth adapter 40 will be comprised of a hydrocarbon polymer having slight deformable characteristics when abutting side 70 of needle adapter 40 contacts abutment surface 35. Upon abutting abutment surface 35 of the autoinjector with abutting side 70 of needle adapter 40, abutting side 70 can deform slightly to dissipate mechanical energy. This deformation is described as slight as only the corner edge between exterior surface 68 and abutting side 70 deforms as is best illustrated in FIG. 5.

Power providing assembly 42 is capable of releasing mechanical energy and thus driving cartridge assembly 36 with needle assembly 50 as well as needle depth adapter 40 toward the proximal end of autoinjector 32. The power providing assembly may extend into the distal portion of housing 34 of autoinjector 32 and is in contact with the distal end of cartridge assembly 36. In one embodiment, the power providing assembly 42 contains a compressed spring which contains the mechanical energy necessary to propel cartridge assembly 36, needle assembly 50, and needle depth adapter 40 toward the proximal end of autoinjector 32.

FIG. 5 illustrates a longitudinal view of the present invention in an actuated condition. Upon actuation, cartridge assembly 36, needle assembly 50, and needle depth adapter 40, are propelled forward toward proximal end 44 of autoinjector 32, preferably under the influence of the compressed spring contained within power providing assembly 42. Specifically, cartridge assembly 36 slides forward within cartridge container 48 thus progressing needle 38 enclosed in punctureable sheath 56 forward for the injection. Preferably, proximal end 44 of autoinjector 32 is placed in close contact with the subject which is to be injected. As needle 38 moves proximately forward, needle 38 punctures punctureable sheath 56 and exits proximal end 44 of autoinjector 32 and subsequently enters the body of the subject at the location where the injection is to be administered. The forward progression of needle 38 is stopped at the point where abutting side 70 needle depth adapter 40 contacts abutting surface 35 at proximal end 44 of autoinjector 32 resulting in needle 38 extending to needle extension length 39. Specifically, abutting surface 35 is comprised of rigid interior shoulders of cartridge container 48 but may also be of housing 34 in other embodiments. Abutting surface 35 is also virtually nonflexible providing a surface so that a precise injection depth can be realized. As such, abutting surface 35 acts as a precise mechanical stop to the forward progression of needle 38 by contacting abutting side 70 of needle depth adapter 40, resulting in a novel autoinjector having a very precise penetration depth. The length of needle extension length 39 of the novel autoinjector 32 is much more precise than the prior art needle length 23 illustrated in FIG. 2, as the deviation from a desired extension length is much smaller through the use of the needle depth adapter of the present invention than is by using the buckling sheath of the prior art.

For example, in administering subcutaneous injections, the needle depth adapter of the present invention provides for a precise pre-determined depth of from about 0.15 inches to about 0.30 inches, and more preferably of from about 0.20 inches to about 0.25 inches. With this precise and advantageously smaller range of potential needle penetration depths, medicaments can be more accurately delivered to an exact location within the subject.

Once needle 38 is fully extended to the needle extension length 39 limited by needle depth adapter 40, power providing assembly 42 forces plunger 60 located within cartridge assembly 36 forward toward the proximal end of autoinjector 32. The movement of plunger 60 applies pressure to the liquid medicament contained within cartridge assembly 36 causing the medicament to exit out through the piercing end of needle 18 at the desired depth within the subject. For example, medicaments such as, but not limited to, sumatriptan, rizatriptan, frovatriptan, zolmitriptan, naratriptan, as well as loperamide hydrochloride can be utilized by the autoinjector of the present invention.

The invention of the present application can be utilized and is preferable for use with medicaments requiring injection at a specific depth within a subject. While the invention can be utilized for both intramuscular and subcutaneous injections, the invention is especially useful for subcutaneous injections wherein medicaments must usually be injected at a much more precise depth. While the preferable range for subcutaneous injections utilizing a needle depth adapter is from about 0.15 inches to about 0.30 inches and more preferably of from about 0.20 inches to about 0.25 inches, the needle depth adapter can be configured in a variety of sizes so as to provide for other precise needle injection depths.

The invention of the present application can be utilized by an individual for self-administration or by another individual on a subject. With the medicament pre-loaded within the autoinjector and the needle being fixed at a specific length with the needle depth adapter providing for a specified injection depth, the autoinjector can be utilized by individuals having very little or no medical training. Furthermore, the simplicity of the autoinjector of the present invention having a fixed needle and predetermined injection depth determined by the needle depth adapter, makes the autoinjector suitable for use in emergency trauma situations wherein prior art autoinjectors may provide erroneous injection depths. Additionally, the punctureable sheath is preferably not removed prior to administering the injection as the needle of the autoinjector of the present invention pierces through the sheath upon activation of the autoinjector. This design adds to the simplicity of use of the autoinjector when compared to many prior art autoinjectors where the sheath must be removed prior to activation of the injector.

Accordingly, by the practice of the present invention, autoinjectors having heretofore unrecognized characteristics are disclosed. These autoinjector embodiments exhibit exceptionally high injection depth precision in administering liquid medicaments to subjects and have design characteristics enabling the autoinjectors to be used by unskilled individuals under the stress of emergency trauma.

The disclosure of all cited patents and publications referred to in the application are incorporated herein by reference.

The above description is intended to enable the person skilled in the art to practice the invention. It is not intended to detail all of the possible variations and modifications that will become apparent to the skilled worker upon reading the description. It is intended, however, that all such modifications and variations be included within the scope of the invention that is defined by the following claims. The claims are intended to cover the indicated elements and steps in any arrangement or sequence that is effective to meet the objectives intended for the invention, unless the context specifically indicates the contrary.

What is claimed is:

1. An autoinjector assembly comprising:
   an outer tube having a distal end and a proximal end, and having an abutment surface defined on the outer tube;
   a cartridge assembly having a distal end and a proximal end, moveably situated within the outer tube;
   a needle attached to the proximal end of the cartridge assembly;
   a punctureable sheath covering the needle with the sheath being nonremovable and maintained within the autoinjector assembly;
   an activateable power providing assembly for providing force to move the cartridge assembly to cause the needle to extend out of the proximal end of the outer tube; and
   a needle depth adapter connected to the proximal end of the cartridge assembly for limiting the extension of the needle out of the proximal end of the outer tube by abutting the abutment surface of the outer tube and thereby providing a depth of injection of from about 0.15 inches to about 0.30 inches; and
   the needle depth adapter having a constant longitudinal length where the longitudinal length is about the same both prior to and after abutting the abutment surface.

2. The injector of claim 1 wherein the depth of injection is from about 0.20 inches to about 0.25 inches.

3. The injector of claim 1 wherein the depth of injection is limited to a range to provide a subcutaneous injection.

4. The injector of claim 1 wherein the needle depth adapter is comprised of a material selected from the group consisting of thermoplastics, polymers, hydrocarbon polymers, deformable metals, cellulosic compositions and combinations thereof.

5. The injector of claim 1 wherein the needle depth adapter is comprised of hydrocarbon polymers.

6. The injector of claim 5 wherein the needle depth adapter is comprised of rubber.

7. The injector of claim 1 wherein the needle depth adapter is deformable.

8. The injector of claim 1 wherein the needle depth adapter further comprises an abutting side, a distal side, a radial exterior surface, and a radial interior surface.

9. The injector of claim 8 wherein the needle depth adapter is positioned so that the abutting side of the needle depth adapter can abut the abutment surface.

10. The injector of claim 8 wherein the distal side is perpendicular to the radial exterior surface.

11. The injector of claim 8 wherein the distal side is perpendicular to the radial interior surface.

12. The injector of claim 8 wherein the abutting side is perpendicular to the radial exterior surface.

13. The injector of claim 8 wherein the needle depth adapter further comprises a length of the radial exterior surface when measured from the distal side to the abutting side that is about equal to the length of the radial interior surface when measured from the distal side to the abutting side.

14. The injector of claim 8 wherein the needle depth adapter further comprises an exterior diameter of from about 0.4 inches to about 0.6 inches.

15. The injector of claim 8 wherein the needle depth adapter further comprises an interior diameter of from about 0.2 inches to about 0.4 inches.

16. The injector of claim 8 wherein the needle depth adapter further comprises a radial thickness measured from the needle depth adapter's radial exterior surface to the needle depth adapter's radial interior surface of from about 0.05 inches to about 0.18 inches.

17. The injector of claim 8 wherein the needle depth adapter further comprises a radial thickness measured from the needle depth adapter's radial exterior surface to the needle depth adapter's radial interior surface, and a ratio of length of the needle depth adapter when measured from the distal side to the abutting side, to the radial thickness of greater than about 2.

18. The injector of claim 1 further comprising the punctureable needle sheath attached to the proximal end of the cartridge assembly.

19. The injector of claim 18 wherein the punctureable needle sheath is collapsible.

20. The injector of claim 18 wherein the sheath is comprised of materials selected from the group consisting of polymers, metals, cellulosic materials, plastics, and combinations thereof.

21. The injector of claim 1 further comprising a medicament contained within the cartridge assembly to be injected out through the needle.

22. The injector of claim 21 wherein the medicament is selected from the group consisting of sumatriptan, rizatriptan, frovatriptan, zolmitriptan, naratriptan, loperamide hydrochloride, and combinations thereof.

23. The injector of claim 21 wherein the medicament is sumatriptan.

24. An autoinjector assembly comprising:
a cylindrical housing having a distal end and a proximal end with a tapered, nonremovable abutment surface;
a cartridge assembly moveably situated within the cylindrical housing including
a rigid cartridge having a distal end and a proximal end; and
a plunger moveably situated within the rigid cartridge;
a needle assembly connected to the proximal end of the rigid cartridge including
a needle having a piercing end and an attachment end;
a needle hub having a first connection point for connecting the needle assembly to the proximal end of the rigid cartridge and a second connection point for receiving the needle's attachment end; and
a nonremovable punctureable sheath over the piercing end of the needle which remains substantially within the autoinjector;
a power assembly received in the distal end of the cylindrical housing for releasing mechanical energy to move the cartridge assembly with connected needle assembly within the cylindrical housing to cause the needle to extend out of the proximal end of the cylindrical housing; and
an annular needle depth adapter received about the needle assembly for limiting the proximal movement of the connected cartridge assembly and needle assembly by abutting the abutment surface resulting in the piercing end of the needle extending to an injection depth; and
the needle depth adapter having a longitudinal length and radial thickness with the longitudinal length being about at least twice as large as the radial thickness.

25. The injector of claim 24 wherein the injection depth is of from about 0.015 inches to about 0.30 inches.

26. The injector of claim 25 wherein the injection depth is of from about 0.20 to about 0.25 inches.

27. The injector of claim 24 wherein the needle depth adapter is comprised of a material selected from the group consisting of thermoplastics, polymers, hydrocarbon polymers, deformable metals, cellulosic compositions and combinations thereof.

28. The injector of claim 24 wherein the needle depth adapter is comprised of at least one hydrocarbon polymer.

29. The injector of claim 24 further comprising a medicament contained within the rigid cartridge.

30. The injector of claim 29 wherein the medicament is selected from the group consisting of sumatriptan, rizatriptan, frovatriptan, zolmitriptan, naratriptan, loperamide hydrochloride, and combinations thereof.

31. The injector of claim 29 wherein the medicament is sumatriptan.

32. A method of administering an injection comprising the steps of:
a) actuating a power assembly and thereby releasing mechanical energy the power assembly in functional contact with a cartridge assembly contained within a cylindrical housing with the cylindrical housing having a distal end and a proximal end;
b) moving a nonremovable needle connected to the cartridge assembly and having a proximally extending piercing end, toward the proximal end of the cylindrical housing so that the piercing end of the needle pierces a sheath and extends from the cylindrical housing; and
c) limiting the proximal movement of the needle by abutment of a needle depth adapter having a longitudinal length and an abutting surface with the cylindrical housing so that the needle extends to an injection depth with a juncture formed between the longitudinal length and the abutting surface of the needle depth adapter partially deforming against the cylindrical housing.

33. The method of claim 32 wherein step a) further comprises actuating the power assembly by self-administration of the injection by a person receiving the injection.

34. The method of claim 32 wherein in step c) the injection depth is from about 0.15 inches to about 0.30 inches.

35. The method of claim 32 wherein step c) further comprises the needle depth adapter deforming from the abutment of the needle depth adapter with the cylindrical housing.

36. The method of claim 32 further comprising injecting a medicament from the piercing end of the needle at the injection depth.

37. The method of claim 36 wherein the medicament is sumatriptan.

38. The method of claim 36 wherein the medicament is selected from the group consisting of sumatriptan, rizatriptan, frovatriptan, zolmitriptan, naratriptan, loperamide hydrochloride, and combinations thereof.

39. The autoinjector assembly of claim 1 wherein the abutment surface is alternatively located on a cartridge container fit to the outer tube.

40. The autoinjector assembly of claim 24 wherein the tapered abutment surface is alternatively located on a cartridge container fit to the cylindrical housing.

41. An autoinjector assembly comprising:
an outer tube having a distal end and a proximal end, and having an abutment surface defined on the outer tube;

a cartridge assembly having a distal end and a proximal end, moveably situated within the outer tube;

a needle attached to the proximal end of the cartridge assembly;

a punctureable sheath covering the needle with the sheath being nonremovable and maintained within the autoinjector assembly;

an activateable power providing assembly for providing force to move the cartridge assembly to cause the needle to extend out of the proximal end of the outer tube; and a needle depth adapter connected to the proximal end of the cartridge assembly for limiting the extension of the needle out of the proximal end of the outer tube by abutting the abutment surface of the outer tube and thereby providing a depth of injection of from about 0.15 inches to about 0.30 inches;

the needle depth adapter having a constant longitudinal length where the longitudinal length is about the same both prior to and after abutting the abutment surface; and the needle depth adapter having a longitudinal length and radial thickness with the longitudinal length being about at least twice as large as the radial thickness.

42. An autoinjector assembly comprising:

an outer tube having a distal end and a proximal end, and having an abutment surface defined on the outer tube;

a cartridge assembly having a distal end and a proximal end, moveably situated within the outer tube;

a needle attached to the proximal end of the cartridge assembly;

a punctureable sheath covering the needle with the sheath being nonremovable and maintained within the autoinjector assembly;

an activateable power providing assembly for providing force to move the cartridge assembly to cause the needle to extend out of the proximal end of the outer tube; and a needle depth adapter connected to the proximal end of the cartridge assembly for limiting the extension of the needle out of the proximal end of the outer tube by abutting the abutment surface of the outer tube and thereby providing a depth of injection of from about 0.20 inches to about 0.30 inches.

43. The autoinjector assembly of claim 42 further comprising a medicament contained within the cartridge assembly to be injected out through the needle.

44. The autoinjector assembly of claim 43 wherein the medicament is selected from the group consisting of sumatriptan, rizatriptan, frovatriptan, zolmitriptan, naratriptan, loperamide hydrochloride, and combinations thereof.

45. The autoinjector assembly of claim 43 wherein the medicament is sumatriptan.

46. The autoinjector assembly of claim 41 further comprising a medicament contained within the cartridge assembly to be injected out through the needle.

47. The autoinjector assembly of claim 46 wherein the medicament is selected from the group consisting of sumatriptan, rizatriptan, frovatriptan, zolmitriptan, naratriptan, loperamide hydrochloride, and combinations thereof.

48. The autoinjector assembly of claim 46 wherein the medicament is sumatriptan.

* * * * *

UNITED STATES PATENT AND TRADEMARK OFFICE
CERTIFICATE OF CORRECTION

| | |
|---|---|
| PATENT NO. | : 7,811,254 B2 |
| APPLICATION NO. | : 11/788823 |
| DATED | : October 12, 2010 |
| INVENTOR(S) | : Wilmot et al. |

It is certified that error appears in the above-identified patent and that said Letters Patent is hereby corrected as shown below:

Column 12, line 26, insert --from-- after "energy".

Signed and Sealed this

Thirtieth Day of November, 2010

David J. Kappos
*Director of the United States Patent and Trademark Office*